(12) United States Patent
Kim et al.

(10) Patent No.: US 12,144,840 B2
(45) Date of Patent: Nov. 19, 2024

(54) METHOD FOR TREATING OR PREVENTING BENIGN PROSTATIC HYPERPLASIA

(71) Applicant: QUBEST BIO CO., LTD., Yongin-si (KR)

(72) Inventors: Kyung-Jae Kim, Guri-si (KR);
Young-Cheon Song, Seoul (KR);
Hyun-Seok Kong, Seoul (KR);
Jin-Man Kim, Yongin-si (KR)

(73) Assignee: QUBEST BIO CO., LTD., Yongin-si (KR)

( * ) Notice: Subject to any disclaimer, the term of this patent is extended or adjusted under 35 U.S.C. 154(b) by 693 days.

(21) Appl. No.: 17/392,498

(22) Filed: Aug. 3, 2021

(65) Prior Publication Data
US 2021/0379133 A1    Dec. 9, 2021

Related U.S. Application Data

(63) Continuation-in-part of application No. 16/621,808, filed as application No. PCT/KR2017/009115 on Aug. 22, 2017, now abandoned.

(51) Int. Cl.
| | |
|---|---|
| *A61K 36/285* | (2006.01) |
| *A23L 33/00* | (2016.01) |
| *A23L 33/10* | (2016.01) |
| *A23L 33/105* | (2016.01) |
| *A61K 31/343* | (2006.01) |
| *A61P 13/08* | (2006.01) |

(52) U.S. Cl.
CPC ............ *A61K 36/285* (2013.01); *A23L 33/10* (2016.08); *A23L 33/105* (2016.08); *A23L 33/40* (2016.08); *A61K 31/343* (2013.01); *A61P 13/08* (2018.01); *A23V 2002/00* (2013.01); *A61K 2236/333* (2013.01)

(58) Field of Classification Search
None
See application file for complete search history.

(56) References Cited

U.S. PATENT DOCUMENTS

| 6,790,464 B2 | 9/2004 | Kuok et al. | |
| 2004/0142001 A1* | 7/2004 | Kuok ..................... | A61K 36/62 424/773 |

FOREIGN PATENT DOCUMENTS

| CN | 101172135 A | 5/2008 |
| CN | 100420481 C | 9/2008 |
| CN | 102716184 A | 10/2012 |
| CN | 102787018 A | 11/2012 |
| CN | 103845689 A | 6/2014 |
| CN | 106237250 A | 12/2016 |
| KR | 10-2014-0038612 A | 3/2014 |

OTHER PUBLICATIONS

"What is Benign Prostatic Hyperplasia (BPH)?" (https://www.urologyhealth.org/urology-a-z/b/benign-prostatic-hyperplasia-(bph))—accessed May 2024.*
Hsu (Journal of Urology (2011), vol. 185, pp. 1967-1974).*
Iqbal, Muzamal, et al., "Phytochemicals as a potential source for TNF-α inhibitors," *Phytochemistry Reviews*, vol. 12, No. 1, 2013 (pp. 65-93).
Rasul, Azhar, et al., "Induction of Apoptosis by Costunolide in Bladder Cancer Cells is Mediated through ROS Generation and Mitochondrial Dysfunction," *Molecules*, 18, 2, 2013 (pp. 1418-1433).
Chen, Yan, et al., "Three statistical experimental designs for enhancing yield of active compounds from herbal medicines and anti-motion sickness bioactivity," *Pharmacognosy magazine*, 11, 43, 2015 (10 pages in English).
Chung, Kyung-Sook, et al., "Anti-Proliferation Effects of Garlic (*Allium sativum* L.) on the Progression of Benign Prostatic Hyperplasia," *Phytotherapy Research*, 30, 7, 2016 (pp. 1197-1203).
Lapan Brittany et al., "MP17-02 TNFα Antagonists Reduce Incidence of BPH in Patients With Autoimmune Inflammatory Conditions", *Journal of Urology*, vol. 197, No. 4 , 2017 (1 page in English).
Morgia, Giuseppe, et al., "Survivin and NAIP in Human Benign Prostatic Hyperplasia: Protective Role of the Association of *Serenoa repens*, Lycopene and Selenium from the Randomized Clinical Study," *International journal of molecular sciences*, 18, 3, 2017 (pp. 1-11).
International Search Report issued on May 21, 2018 in counterpart International Patent Application No. PCT/KR2017/009115 (2 pages in English and 2 pages in Korean).
Japanese Office Action issued on Dec. 1, 2020 in counterpart Japanese Patent Application No. 2020-591966 (4 pages in English and 4 pages in Japanese).
Extended European Search Report issued on Feb. 24, 2021 in counterpart European Patent Application No. 17922675.8 (7 pages in English).

* cited by examiner

*Primary Examiner* — Susan Hoffman
(74) *Attorney, Agent, or Firm* — NSIP Law (57) ABSTRACT

The present invention relates to a method for treating or preventing benign prostatic hyperplasia comprising administering an effective amount of a composition consisting essentially of an Aucklandiae Radix extract as an active ingredient to a subject in need of treating or preventing benign prostatic hyperplasia.

4 Claims, 4 Drawing Sheets

METHOD FOR TREATING OR PREVENTING BENIGN PROSTATIC HYPERPLASIA

CROSS-REFERENCE TO RELATED APPLICATIONS

This application is a continuation-in-part of U.S. patent application Ser. No. 16/621,808 filed on Dec. 12, 2019, which is a U.S. National Stage Application of International Application No. PCT/KR2017/009115, filed on Aug. 22, 2017, the entire disclosures of which are incorporated herein by reference for all purposes.

TECHNICAL FIELD

The present invention relates to a method for treating or preventing benign prostatic hyperplasia.

BACKGROUND ART

Aucklandiae Radix is the root of *Aucklandia lappa* Decne, a perennial herb of the family Asteraceae. Aucklandiae Radix (is described in herb medicines listed in the Korean Herbal Pharmacopoeia (KHP), and also described in oriental medical books, such as *Donguibogam, Bangyakhappyeon*, and *Bencaogangmu*.

The currently distributed Aucklandiae Radix is a cultivation product of *A. lappa*, which is not grown in Korea but is cultivated in Yunnan, Guangxi, and Sichuan in China. Aucklandiae Radix is distributed under name of Aucklandiae *Lappa radix* or *Saussurea radix* depending on the cultivation region, but these are merely different names of Aucklandiae Radix and are originated from the identical *A. lappa*. In Korea, the roots of *Inula helenium* L. (having the same plant name as Aucklandiae Radix) of the family Asteraceae are called Helenii Radix, and *Inula helenium* L. is listed separately from *A. lappa* in the Korean Pharmacopoeia. Helenii Radix has been used as a substitute for Aucklandiae Radix, but is known to lack marketability.

The roots of *Vladimiria souliei* (Franck) Ling, which is another plant of the family Asteraceae, are also distributed under the name of Vladimiriae Radix in Chinese medicinal stuffs markets, and the roots of *Aristolochia contorta* Bunge of the family *Aristolochia* are also distributed under the name of *Aristolochia* Radix as a mixed product or a fake product of Aucklandiae Radix. However, these are banned in Korea due to differences in the composition and contents of bioactive compounds from Aucklandiae Radix.

Aucklandiae Radix contains 0.3-2.78% of essential oil, and is an herb medicine containing 1.8% or more of a sum of costunolide ($C_{15}H_{20}O_2$: 232.32) and dehydrocostus lactone ($C_{15}H_{18}O_2$: 230.30) as main components. Aucklandiae Radix has aromatic stomachic, diuretic, apophlegmatic, and anthelmintic actions, and thus has been used for gastrointestinal disorders, such as indigestion, vomiting, vomiting and diarrhea, and diarrhea.

Especially, costunolide, which is one of the main components, belongs to terpene-based sesquiterpene lactones, and has been traditionally used as various therapeutic materials, such as antiinflammatory, antibacterial, and antiviral materials. Costunolide acts a strong antioxidant action of preventing vascular oxidation by blocking the activity of nitric oxide synthase. Costunolide is a substance that a plant produces to protect itself from oxidation stress, such as ultraviolet light or harmful insect damage, and also costunolide seems to perform similar actions in the human body. It has been recently reported that costunolide also has anticancer effects of preventing growth, angiogenesis, and metastasis of various cancer cell lines.

The prostate is a gland organ that is 4×3×3 $cm^3$ in size and about 20 ml in volume, has a form in which fibromuscular tissue surrounds glandular tissue, and is located below the male bladder. The prostate grows 1.6 g every year to an adult size until the late 20s after the second sexual aging, and grows 0.4 g every year from the late 30s.

Benign prostatic hyperplasia is a disease that causes lower urinary tract obstruction or the like, accompanied by nodular hyperplasia and hypertrophy of prostate tissue due to increasing levels of dihydrotestosterone (DHT) together with relatively decreasing levels of testosterone in the body after the middle age, and 5-alpha reductase plays an important role in increasing DHT in the prostate tissue.

Endogenously, the apoptosis inhibiting gene survivin has been reported to increase and bcl-1 is known to be increasingly expressed in the prostate tissue in prostate cancer and benign prostatic hyperplasia, and therefore, through such a pathological mechanism, the prostate tissue overgrows, clinically resulting in various urination-related symptoms, such as urinary obstruction, a feeling of residual urine, urinary instability, difficulty in urination, and dysuria, and in severe cases, causing complications, such as calculosis, renal failure, hematuria, and infection.

Especially, benign prostatic hyperplasia has a great influence on the quality of life of the male population with the increase of the elderly population. In recent years, with the improvement of economic and social conditions, the attitude to the importance of benign prostatic hyperplasia is changing and the markets of therapeutics therefor are also expanding.

Until now, alpha adrenergic receptor blockers that perform symptom amelioration including urination improvement, 5-alpha reductase inhibitors that lower DHT levels, and some complementary and alternative therapies have been mainly used for benign prostatic hyperplasia, but the curative options were limited.

The alpha adrenergic receptor blockers include terazosin, doxazosin, alfuzosin, tamsulosin, and the like, and the 5-alpha reductase inhibitors include finasteride, dutasteride, and the like. Despite therapeutic benefits, these medicines have significant restrictions in their use due to the inherent adverse reactions thereof. For instance, the alpha adrenergic receptor blockers cause orthostatic hypertension and cardiovascular side effects, and the 5-alpha reductase inhibitors cause sides effects, such as decrease of sexual desire. For these reasons, complementary and alternative medicines have been proposed as alternatives, and saw palmetto or the like is frequently used. However, these medicines have limited effects, for example, the related academies in Korea suggested on the basis of oversea research results that such medicines are negative about benign prostatic hyperplasia relief effects, and therefore, there is a need for new therapeutically effective substances.

Up to now, nothing is known about the effects of the Aucklandiae Radix extract, which contains costunolide as an active ingredient and is noted by the present inventors, on the treatment of benign prostatic hyperplasia. The present inventors verified through cell tests and prostate-induced animal tests that the above ingredient has no hepatotoxicity and cytotoxicity but enhances immunity and decreases the prostate weight and volume, alleviating thickened prostate, and thus completed the present invention.

DETAILED DESCRIPTION OF THE INVENTION

Technical Problem

The present invention has been made in view of the above-mentioned problems, and an aspect of the present invention is to provide a composition capable of being applied to benign prostatic hyperplasia by verifying that Aucklandiae Radix extract has an effect on benign prostatic hyperplasia.

Technical Solution

In accordance with an aspect of the present invention, there is provided a composition containing an Aucklandiae Radix extract as an active ingredient for treatment and prevention of benign prostatic hyperplasia.

The Aucklandiae Radix extract may be obtained using any one of ethanol, methanol, and water as a solvent.

In accordance with another aspect of the present invention, there is provided a composition containing costunolide as an active ingredient for treatment and prevention of benign prostatic hyperplasia.

In accordance with still another aspect of the present invention, there is provided a health functional food containing the Aucklandiae Radix extract or costunolide for alleviation of benign prostatic hyperplasia.

In accordance with still another aspect of the present invention, there is provided a method for treating or preventing benign prostatic hyperplasia including administering an effective amount of a composition consisting essentially of an Aucklandiae Radix extract as an active ingredient to a subject in need of treating or preventing benign prostatic hyperplasia.

The Aucklandiae Radix extract may be obtained using any one of ethanol, methanol, and water as a solvent.

In accordance with still another aspect of the present invention, there is provided a method for treating or preventing benign prostatic hyperplasia including administering an effective amount of a composition consisting essentially of costunolide as an active ingredient to a subject in need of treating or preventing benign prostatic hyperplasia.

In accordance with still another aspect of the present invention, there is provided a method for treating or preventing benign prostatic hyperplasia including administering an effective amount of a food composition consisting essentially of Aucklandiae Radix extract or costunolide as an active ingredient to a subject in need of treating or preventing benign prostatic hyperplasia.

Advantageous Effects

As set forth below, the Aucklandiae Radix extract according to the present invention has an effect on benign prostatic hyperplasia.

MODE FOR CARRYING OUT THE INVENTION

Hereinafter, the present disclosure will be described in more detail.

As used herein, "prevention" refers to any action of inhibiting or delaying the onset of benign prostatic hyperplasia by administrating the composition or food composition according to the present disclosure. In addition, it includes treatment of a subject with remission of the disease for the prophylaxis and the prevention of recurrence.

As used herein, "treatment" refers to any action that improves or beneficially alters the condition, such as alleviating, reducing, or eliminating the onset of benign prostatic hyperplasia by administrating the composition or the food composition according to the present disclosure.

As used herein, "improvement" refers to any action of that improves or beneficially alters benign prostatic hyperplasia by ingestion of the composition or the food composition according to the present disclosure.

As used herein, "composition" means a composition administered for a specific purpose, and for the purposes of the present disclosure, it refers to be administered to prevent or treat benign prostatic hyperplasia.

As used herein, "food composition" has a meaning similar to food for specified health use (FoSHU), and refers to foods with high medical and medicinal effects processed so that the biological regulation function is effectively shown in addition to nutritional supply.

The composition and food composition for preventing or treating benign prostatic hyperplasia according to the present disclosure may comprise "Aucklandiae Radix."

As used herein, the term "Aucklandiae Radix" encompasses Aucklandiae *Lappa radix*, Helenii Radix, Vladimiriae Radix, and the like in the present disclosure.

As used herein, the term "consisting essentially of" means that the composition or food composition includes the specified materials and those that do not materially affect the basic and novel characteristics of the composition or food composition, such as carriers, excipients, disintegrants, sweeteners, coating agents, swelling agents, lubricants, slip modifiers, flavors, antioxidants, buffers, bacteriostats, diluents, dispersants, surfactants, binders and lubricants, which are conventionally used for the preparation of the pharmaceutical composition, but not limited thereto.

As used herein, the term "effective amount" refers to an amount sufficient to treat a disease at a reasonable benefit/risk ratio applicable to medical treatment and does not cause side effects, and the effective dose level can be determined according to factors including the patient's health status, type of disease, severity of disease, activity of the drug, sensitivity to the drug, method of administration, time of administration, route of administration and rate of excretion, duration of treatment, drugs used in combination or concurrently, and other factor well known in the medical field.

In the food composition according to the present disclosure, the food composition may be prepared in various forms such as capsules, tablets, granules, powders, suspensions or syrups.

The food composition may contain various nutrients, vitamins, minerals (electrolytes), flavors such as synthetic flavors and natural flavors, etc., colorants and fillers (cheese, chocolate etc.), pectic acid and its salts, alginic acid and its salts, organic acids, protective colloid thickeners, pH adjusting agents, stabilizers, preservatives, glycerin, alcohols, carbonating agents used in carbonated drinks, and the like. It may also contain flesh for the production of natural fruit juices, synthetic fruit juices and vegetable drinks. These components may be used independently or in combination.

The food composition may be in the form of any one of dairy products, bread, confectionery, ice cream, beverage, tea, functional water and vitamin complex.

In addition, the food composition may further include a food additive and compliance as a food additive is determined by the standards for the applicable item in accordance with General Regulations and General Test Methods of Korean Food Additives Codex approved by the Ministry of Food and Drug Safety, unless otherwise provided.

Examples of the items published in the above-mentioned "Korean Food Additives Codex" include chemical synthetics such as ketones, glycine, potassium citrate, nicotinic acid, and cinnamic acid and the like, natural additives such as persimmon color, licorice extract, crystalline cellulose, kaoliang color and guar gum and the like, mixed preparations such as L-sodium glutamate preparation, alkaline agents for noodles, preservative formulation and a tar color formulation and the like.

According to one embodiment of the present disclosure, the composition or food composition may be administered intravenously, intraarterially, intraperitoneally, intramuscularly, intrasternally, transdermally, nasally, inhaled, topically, rectally, orally, intraocularly or intradermally to the subject in the conventional manner.

The preferred dosage of the composition or food composition may vary depending on the condition and weight of the subject, the type and extent of the disease, the drug form, the route of administration, and the duration, and may be appropriately selected by those skilled in the art. The composition or food composition may be administered once a day or divided into several times, and the scope of the invention is not limited thereto.

In the present disclosure, the 'subject' may be a mammal including a human, but it is not limited thereto.

Hereinafter, the present invention will be described in detail with reference to examples. The examples are provided merely to help with the understanding of the present invention, and the scope of the present invention is not limited to the examples.

<1. Manufacture of Aucklandiae Radix Extracts>

Aucklandiae Radix used in the present tests was purchased from Hunjin Pharmacy.

The purchased Aucklandiae Radix was subjected to extraction a total of twice using a reflux extractor (COSMOS660/80L, Misung Scientific. co. Ltd., Yangju, Kyunggido, Korea), and then the extracts were used in mixture. A solvent was added at 10 times the weight of the sample at the first extraction and added at 7 times the weight of the sample at the second extraction, followed by heat extraction for 3 hours each time of extraction.

The extracts were filtered (Whatman No 2, Maidstone, England), lyophilized (PVTFD10R, Ilsinb iobase, Doundu-cheon, Gyeonggido, Korea), milled (Cyclotec 1093 Sample Mill, Tecator Co., Sweden), and then stored frozen at −20° C. before use.

As the solvent, 100% methanol, 70% ethanol, or 30% ethanol was used, and the extraction conditions were identical therefor.

<2. HPLC Analysis of Aucklandiae Radix Extract>

The Aucklandiae Radix extracts were weighed 10 mg, respectively, and shaken to dissolve in methanol for 30 minutes or longer. The undissolved components were removed through a membrane filter (0.45 μm), and only the clear solution was subjected to HPLC analysis in the above conditions to obtain chromatograms, and the obtained results were summarized into a table (Table 1). The approximate concentrations were calculated by inserting each peak area from the chromatograms into the calibration equation, and the results verified that compared with the 30% ethanol extract, the 70% ethanol extract contained costunolide by about 1.8-fold and dehydrocostus lactone by about 1.6-fold.

TABLE 1

| EtOH extract | Concentration (ug/mL) | |
| --- | --- | --- |
| | Costunolide | Dehydrocostuslactone |
| a) 30% extract | 80.0 (100%) | 106.4 (100%) |
| b) 70% extract | 145.4 (182%) | 165.1 (155%) |

<3. Evaluation of Antiinflammatory Effect of Aucklandiae Radix Extracts and Costunolide>

1) Culture of Macrophages

RAW 264.7 cells, which were macrophages used in the present tests, were available from American Type Culture Collection (ATCC). These cells were cultured in $CO_2$ incubator (Formascientific, Inc.) using DMEM containing 10% fetal bovine serum (FBS). The differentiation of cells was observed through microscopic observation, and then the cells were used in the tests.

2) Evaluation of Nitric Oxide (NO) Change and Antiinflammatory Effect

To induce the activation of macrophages, RAW 264.7 cells were treated with 200 ng/ ㎖ lipopolysaccharide (LPS) while simultaneously treated with various concentrations (μg/ ㎖) of a 100% methanol extract of Aucklandiae Radix (expressed by MeOH 100%), a 30% ethanol extract of Aucklandiae Radix (expressed by EtOH 30%), and a 70% ethanol extract of Aucklandiae Radix (expressed by EtOH 70%), and costunolide, and then the cells were cultured in a 37° C., 5% $CO_2$ incubator for 18 hours. After 18 hours, 100 ㎕ of the supernatant was transferred to a new plate for each group, and 100 ㎕ of a solution, in which Griess reagent A (2% sulfanilamide in 5% phosphoric acid) and Greiss reagent B (0.2% naphthylethylenediamine dihydrochloride) were mixed at a rate of 1:1, was added thereto. Thereafter, the absorbance was measured at 540 nm.

Figure 1:
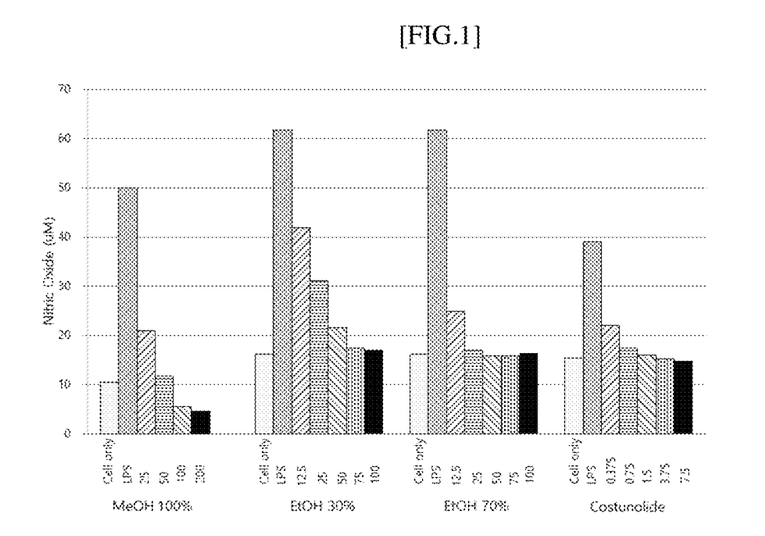
FIG. 1 shows the evaluation results of NO production rate and antiinflammatory effect according to the treatment with a 100% methanol extract of Aucklandiae Radix, a 30% ethanol extract of Aucklandiae Radix, a 70% ethanol extract of Aucklandiae Radix, and costunolide.

As a test result, the amount of NO was increased in the cell only treatment groups as the control groups rather than the LPS alone treatment groups, and the amount of NO was dose-dependent and was significantly decreased in all the groups treated with the Aucklandiae Radix extracts and costunolide (FIG. 1). It can be verified from these results that the Aucklandiae Radix extracts and costunolide had an anti-inflammatory effect of preventing tissue damage by suppressing excessive inflammation of cells.

3) Evaluation of Inflammatory Cytokine Changes and Antiinflammatory Effect

RAW 264.7 cells were treated with 200 ng/mℓ LPS while simultaneously treated with various concentrations (μg/mℓ) of Aucklandiae Radix extracts (EtOH 30% and 70%) and costunolide, and then the cells were cultured in a 37° C., 5% $CO_2$ incubator for 18 hours. After 18 hours, ELISA analysis kits (eBioScience 88-7013, 88-7064 USA, BD 555268 USA) were used to check the levels of the inflammatory cytokines IL-1β, IL-6, and TNF-α in the supernatant of each group.

Figure 2A:
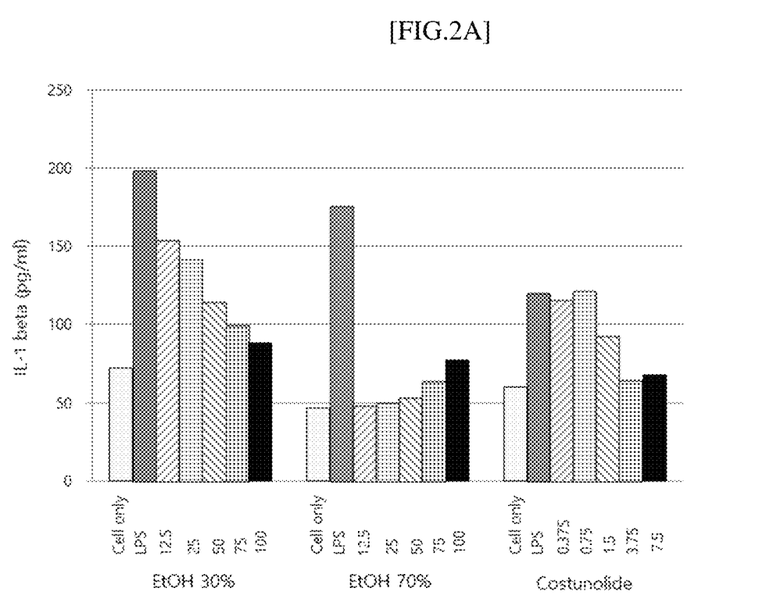
FIGS. 2a, 2b, and 2c show the measurement results of levels of inflammatory cytokines (IL-1β, IL-6, TNF-α) according to the treatment with a 30% ethanol extract of Aucklandiae Radix, a 70% ethanol extract of Aucklandiae Radix, and costunolide.
Figure 2B:
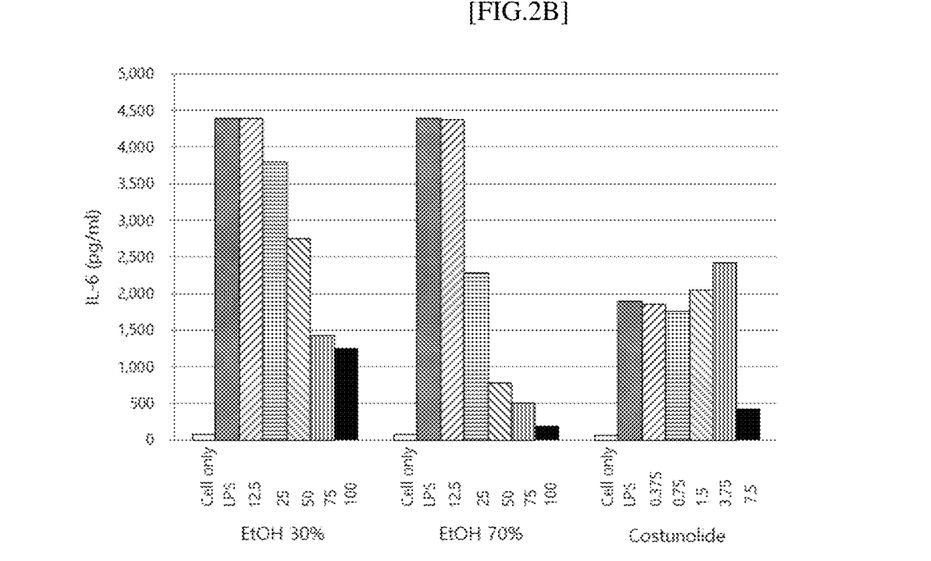
Figure 2C:
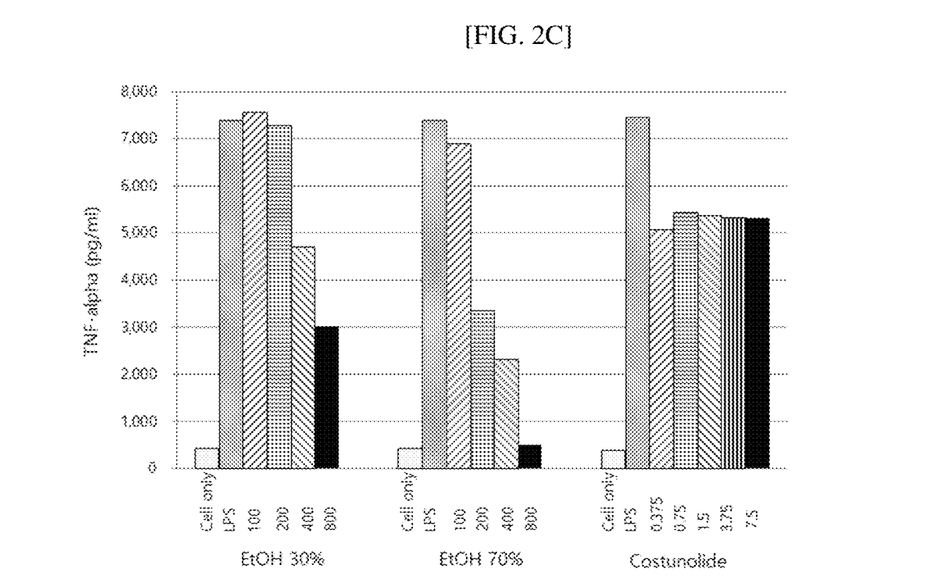

FIG. 2 shows the measurement results through the ELISA analysis kit of the levels of the inflammatory cytokines IL-1β (FIG. 2a), IL-6 (FIG. 2b), and TNF-α (FIG. 2c) in the cultures of macrophages activated by LPS. When compared with the cells treated with only LPS, the cells treated with the Aucklandiae Radix extracts and costunolide showed decreases in the secretion levels of the inflammatory cytokines, indicating that the Aucklandiae Radix extracts and costunolide had an antiinflammatory effect.

<4. Evaluation of Effect of Aucklandiae Radix Extract on Alleviation of Benign Prostatic Hyperplasia>

1) Construction of Benign Prostatic Hyperplasia Animal Models

After 6-week-old male Wistar rats (Samtako, Korea) were obtained and acclimated for one week, six animals constituted each test group when each animal weighed 340-350 g.

As for the test configuration, the animals were divided into groups without testicle removal and groups undergoing 4-hour recovery after testicle removal, and each group was subcutaneously injected with 5 mg/kg testosterone to induce benign prostatic hyperplasia for weeks (BPH induced group). Test groups were constructed by oral administration of Aucklandiae Radix extracts and costunolide at different concentrations (mg/kg) once a day, seven times a week, for 8 weeks. Positive control groups were used by oral administration of finasteride, which has been used as a medicine for benign prostatic hyperplasia.

2) Changes in Prostate Weight and Volume

After the completion of the test, the rats of all the test groups were euthanized, and then prostate tissue and main organs were extracted, and weights and volumes thereof were measured using an electronic scale for animal weights and a caliper ($mm^3$) (Table 2).

The results verified that compared with the normal control groups, the BPH induced groups showed significantly increased weights and volumes, indicating the introduction of benign prostatic hyperplasia.

Figure 3:
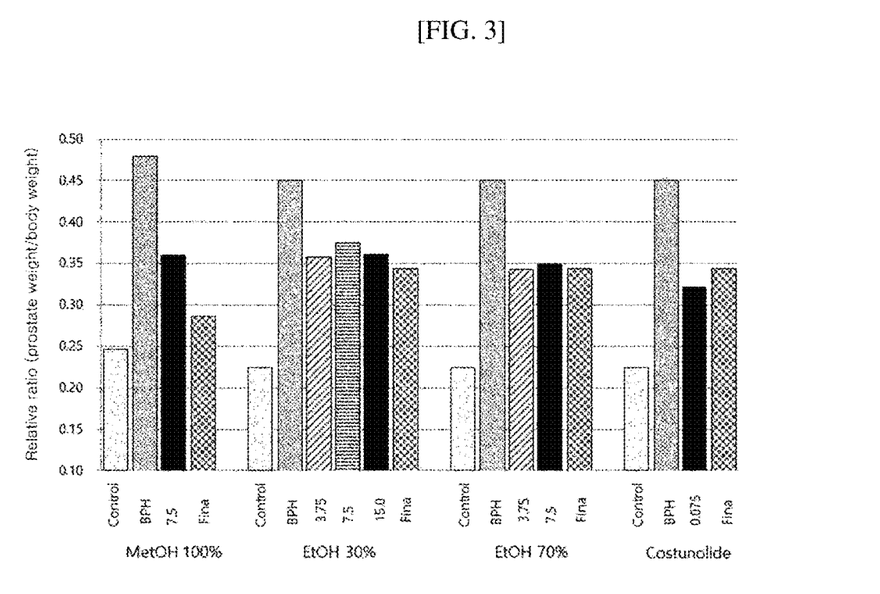
FIG. 3 shows benign prostatic hyperplasia alleviation effect according to the treatment with a 100% methanol extract of Aucklandiae Radix, a 30% ethanol extract of Aucklandiae Radix, a 70% ethanol extract of Aucklandiae Radix, and costunolide.

The prostate weights and volumes of the Aucklandiae Radix extract administration groups were all decreased to similar values to those of finasteride (BPH medicine) administration groups (Fina), and especially, the costunolide administration groups (0.075 μg/mℓ) showed a significant reduction effect compared with the finasteride administration groups (FIG. 3).

TABLE 2

[weight: g, volume $mm^3$]

| Administered material | Test group | Body Weight (a) | Prostate Weight (b) | Ratio (b/a* 100) | Prostate volume | Liver weight | Speen weight |
| --- | --- | --- | --- | --- | --- | --- | --- |
| MeOH | control | 391 | 0.97 | 0.25 | 2,353 | 0.33 | 0.71 |
| | BPH | 384 | 1.82 | 0.48 | 6,145 | 0.13 | 0.64 |
| | 7.5 mg/kg | 377 | 1.37 | 0.36 | 3,530 | 0.11 | 0.65 |
| | Fina | 379 | 1.23 | 0.29 | 2,322 | 0.12 | 0.60 |
| EtOH 30 | control | 489 | 1.09 | 0.22 | 2,952 | 11.28 | 0.72 |
| | BPH | 414 | 1.87 | 0.45 | 6,079 | 9.57 | 0.62 |
| | 3.75 mg/kg | 439 | 1.57 | 0.36 | 4,820 | 9.55 | 0.67 |
| | 7.5 mg/kg | 419 | 1.57 | 0.38 | 4,864 | 10.14 | 0.66 |
| | 15 mg/kg | 411 | 1.47 | 0.36 | 4,443 | 9.86 | 0.72 |
| | Fina | 415 | 1.42 | 0.34 | 4,255 | 9.46 | 0.70 |
| EtOH 70 | control | 489 | 1.09 | 0.22 | 2,952 | 11.28 | 0.72 |
| | BPH | 414 | 1.87 | 0.45 | 6,079 | 9.57 | 0.62 |
| | 3.75 mg/kg | 420 | 1.44 | 0.34 | 4,322 | 10.07 | 0.65 |
| | 7.5 mg/kg | 420 | 1.46 | 0.35 | 4,394 | 9.33 | 0.62 |
| | | 415 | 1.42 | 0.34 | 4,255 | 9.46 | 0.70 |
| costunolide | control | 489 | 1.09 | 0.22 | 2,952 | 11.28 | 0.72 |
| | BPH | 414 | 1.87 | 0.45 | 6,079 | 9.57 | 0.62 |
| | 0.075 mg/kg | 433 | 1.40 | 0.32 | 4,126 | 10.72 | 0.62 |
| | Fina | 415 | 1.42 | 0.34 | 4,255 | 9.46 | 0.70 |

3) Measurement of Hepatotoxicity and Kidney Function Change

For analysis of biochemical markers in serum, blood was obtained through the abdominal vein from rats of all the groups at necropsy. The blood was coagulated for about 30 minutes, and then centrifuged for 5 minutes at 10,000 rpm to separate serum. After serum separation, a biochemistry analyzer (AU480, Beckman Coulter, USA) was used to check liver function (AST, ALP), lipoprotein (total cholesterol (T-CHO)), HDL cholesterol (HDL-C), LDL cholesterol (LDL-C)), and kidney function (creatine) levels (Table 3). The results verified that all the groups administered with the extracts and costunolide showed no significant changes, indicating no hepatotoxicity and kidney toxicity.

TABLE 3

| Administered material | Test group | AST (U/L) | ALP (U/L) | T-CHO (mg/dL) | HDL (mg/dL) | LDL (mg/dL) | CRE (mg/dL) |
|---|---|---|---|---|---|---|---|
| MeOH | control | 77.20 | 32.60 | 59.20 | 19.40 | 16.00 | 0.40 |
| | BPH | 107.60 | 43.80 | 60.20 | 19.60 | 14.40 | 0.30 |
| | 7.5 mg/kg | 105.80 | 51.40 | 67.60 | 21.60 | 17.20 | 0.28 |
| | Fina | 88.20 | 37.20 | 59.00 | 19.20 | 13.20 | 0.30 |
| EtOH 30 | control | 96.00 | 91.50 | 93.33 | 60.00 | 12.67 | 0.37 |
| | BPH | 125.17 | 85.67 | 88.17 | 56.17 | 13.50 | 0.35 |
| | 3.75 mg/kg | 89.00 | 71.33 | 66.50 | 43.00 | 10.67 | 0.30 |
| | 7.5 mg/kg | 121.67 | 86.33 | 79.50 | 50.00 | 12.67 | 0.35 |
| | 15 mg/kg | 145.00 | 70.83 | 86.33 | 55.00 | 13.00 | 0.32 |
| | Fina | 80.67 | 81.50 | 70.83 | 43.83 | 13.67 | 0.27 |
| EtOH 70 | control | 96.00 | 91.50 | 93.33 | 60.00 | 12.67 | 0.37 |
| | BPH | 125.17 | 85.67 | 88.17 | 56.17 | 13.50 | 0.35 |
| | 3.75 mg/kg | 90.33 | 67.67 | 73.00 | 47.17 | 12.50 | 0.28 |
| | 7.5 mg/kg | 70.50 | 64.33 | 71.83 | 47.67 | 12.00 | 0.30 |
| | Fina | 80.67 | 81.50 | 70.83 | 43.83 | 13.67 | 0.27 |
| costunolide | control | 96.00 | 91.50 | 93.33 | 60.00 | 12.67 | 0.37 |
| | BPH | 125.17 | 85.67 | 88.17 | 56.17 | 13.50 | 0.35 |
| | 0.075 mg/kg | 78.33 | 61.17 | 79.67 | 51.50 | 13.17 | 0.27 |
| | Fina | 80.67 | 81.50 | 70.83 | 43.83 | 13.67 | 0.27 |

4) Prostate Pathology Biopsy

After the completion of the test, the prostate tissue extracted from each group was fixed with 10% neutral formalin and stored. The tissue of each group was processed into paraffin blocks, and slides for microscopic inspection of tissue were manufactured and stained with hematoxylin & eosin (H&E). The microscopic inspection of tissue was conducted through a microscope (Olympus, Tokyo, Japan) at a magnification of X200.

Figure 4:
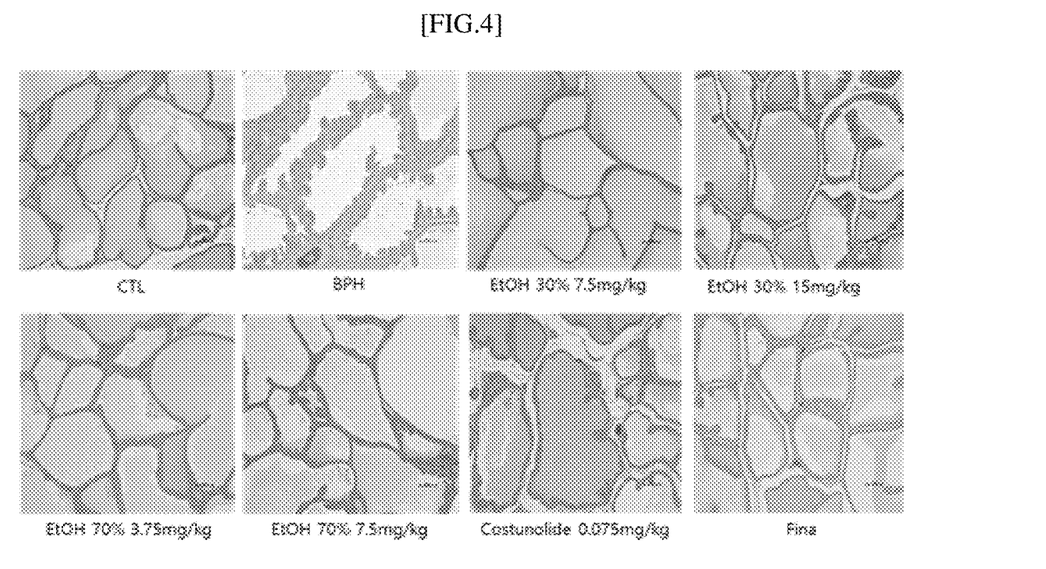
FIGS. 4 and 5 show the results of prostate pathology biopsy according to the Aucklandiae Radix extracts and costunolide.
Figure 5:
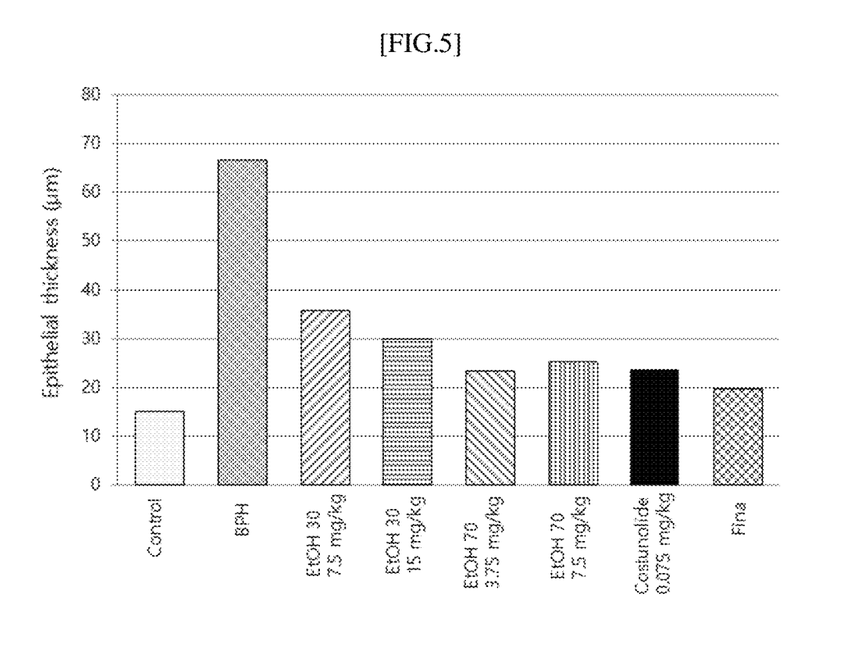

It can be seen that compared with the normal control groups, the benign prostatic hyperplasia induced groups showed atrophy and hypertrophy of epithelial cells of prostate vesicles and overall thickening of the basement membrane. The test groups administered with Aucklandiae Radix extracts and costunolide showed alveolar glands maintained in a round shape without atrophy similar to the normal control group, and showed significantly reduced endothelial thicknesses compared with the benign prostatic hyperplasia induced group (FIGS. 4 and 5).

<5. Evaluation of Toxicity of Aucklandiae Radix Extracts>

For investigation of a safety area of the Aucklandiae Radix extracts, the acute toxicity test and MTD toxicity test were carried out.

For the acute toxicity test, 7-week-old healthy male and female SD rats were divided into one normal control group and two drug administration groups (two groups orally administered with the Aucklandiae Radix extract at a single dose of 1,000 mg and 2,000 mg per kg of body weight), and five animals were taken for each group, and then tested. As a test result, there were no significant differences in body weight, feed intake, and the like between the normal control group and the drug administration groups, and no toxicity-related clinical signs were observed (Table 4: Acute toxicity test results).

TABLE 4

| | | Male | | | | Female | | | |
|---|---|---|---|---|---|---|---|---|---|
| | | B.W. (g) | | | C.S.* | B.W. (g) | | | C.S.* |
| Group | N | Day 1 | Day 7 | Day 14 | Day 14 | Day 1 | Day 7 | Day 14 | Day 14 |
| Control | 5 | 210 ± 9 | 240 ± 13 | 283 ± 18 | No sign | 178 ± 11 | 193 ± 8 | 216 ± 11 | No sign |
| 1000 mg/kg | 5 | 208 ± 10 | 247 ± 10 | 285 ± 12 | No sign | 177 ± 10 | 195 ± 10 | 214 ± 15 | No sign |
| 2000 mg/kg | 5 | 207 ± 11 | 242 ± 13 | 285 ± 16 | No sign | 175 ± 9 | 193 ± 6 | 208 ± 9 | No sign |

Body weight, feed intake, and clinical signs: no significant differences between normal control group and Aucklandiae Radix extract administration groups
C.S.*: Clinical sign For the MTD toxicity test, 7-week-old healthy male and female SD rats were divided into two medicine administration groups (two groups orally administered with 30% and 70% ethanol extracts of the Aucklandiae Radix extract for 5 days), and three animals were taken for each group, and then tested. As a test result, there were no significant differences in body weight, feed intake, and the like between the medicine administration groups, and no toxicity-related signs were observed in clinical testing and necropsy (Table 5: MTD toxicity test results).

TABLE 5

| Group | Male (mg/kg/day) | N | B.W. (g) Day 1 | B.W. (g) Day 3 | B.W. (g) Day 5 | C.S.* Day 1-5 | N.F.** Day 1 - 5 |
|---|---|---|---|---|---|---|---|
| KSB 30% EtOH | 1000 × 5days | 3 | 222 ± 7 | 232 ± 7 | 248 ± 6 | No change | No change |
| KSB 70% EtOH | 1000 × 5days | 3 | 220 ± 4 | 231 ± 4 | 244 ± 2 | No change | No change |

Body weight, feed intake, and clinical signs: no significant differences between two groups.
C.S.*: Clinical Sign,
N.F.**: Necropsy Findings It can be seen from the above results that Aucklandiae Radix extracts can alleviate the thickened prostate by increasing immune-related antiinflammatory responses and reducing prostate weight and volume without general toxicity.

The invention claimed is:

1. A method for treating benign prostatic hyperplasia comprising administering an effective amount of a composition consisting essentially of an Aucklandiae Radix extract as an active ingredient to a subject in need of treating or preventing benign prostatic hyperplasia.

2. The method of claim 1, wherein the Aucklandiae Radix extract is obtained using any one of ethanol, methanol, and water as a solvent.

3. A method for treating benign prostatic hyperplasia comprising administering an effective amount of a composition consisting essentially of costunolide as an active ingredient to a subject in need of treating or preventing benign prostatic hyperplasia.

4. A method for treating benign prostatic hyperplasia comprising administering an effective amount of a food composition consisting essentially of Aucklandiae Radix extract or costunolide as an active ingredient to a subject in need of treating benign prostatic hyperplasia.

* * * * *